(12) United States Patent
Futterknecht

(10) Patent No.: US 6,488,660 B1
(45) Date of Patent: Dec. 3, 2002

(54) INJECTOR FOR APPLYING FLUIDS, ESPECIALLY CONTRAST AGENTS IN X-RAY AND NUCLEAR SPIN TOMOGRAPHY

(75) Inventor: Hans-Dieter Futterknecht, Ulm (DE)

(73) Assignee: Ulrich GmbH & Co. KG, Ulm (DE)

( * ) Notice: Subject to any disclaimer, the term of this patent is extended or adjusted under 35 U.S.C. 154(b) by 0 days.

(21) Appl. No.: 09/646,251
(22) PCT Filed: Nov. 27, 1999
(86) PCT No.: PCT/DE99/03795
§ 371 (c)(1), (2), (4) Date: Sep. 13, 2000
(87) PCT Pub. No.: WO00/41751
PCT Pub. Date: Jul. 20, 2000

(30) Foreign Application Priority Data

Jan. 13, 1999 (DE) .......................... 199 00 936

(51) Int. Cl.$^7$ ................................. A61M 1/00
(52) U.S. Cl. .......................... 604/129; 604/81
(58) Field of Search .............. 604/129, 35, 65, 604/67, 81, 123, 140, 141, 143, 150, 151–155, 246, 247, 248, 250, 252; 417/63

(56) References Cited

U.S. PATENT DOCUMENTS

| | | | |
|---|---|---|---|
| 3,677,248 A | | 7/1972 | McPhee |
| 3,731,679 A | * | 5/1973 | Wilhelmson et al. ........ 604/121 |
| 4,369,780 A | * | 1/1983 | Sakai .......................... 604/123 |
| 4,710,166 A | * | 12/1987 | Thompson et al. ........... 604/81 |
| 4,798,590 A | * | 1/1989 | O'Leary et al. ............. 604/153 |
| 4,838,856 A | * | 6/1989 | Mulreany et al. ............. 604/65 |
| 5,800,383 A | * | 9/1998 | Chandler et al. ............. 604/35 |
| 5,814,004 A | * | 9/1998 | Tamari ........................ 604/6.1 |

FOREIGN PATENT DOCUMENTS

| | | |
|---|---|---|
| FR | 2163893 | 7/1993 |
| WO | 96/40330 | * 12/1996 |
| WO | 97/45150 | 12/1997 |

* cited by examiner

Primary Examiner—Henry Bennett
Assistant Examiner—Quang T Van
(74) Attorney, Agent, or Firm—Herbert Hubno

(57) ABSTRACT

The injector according to the invention serves for applying contrast media for X-ray and nuclear spin tomography and has a tube system (5) consisting of connection tubes (6) and a pump tube (7), as well as several storage vessels (4), each connected via one of the connection tubes (6) as well as a branching piece (8) to a pump tube (7) leading to a cannula. To each connection tube (6) a gas bubble detector (15) as well as a valve (11) are assigned, whereby further to the pump tube (7) a pumping organ (16) reversing the fluid flow from the storage vessel (4) to the cannula is assigned.

14 Claims, 5 Drawing Sheets

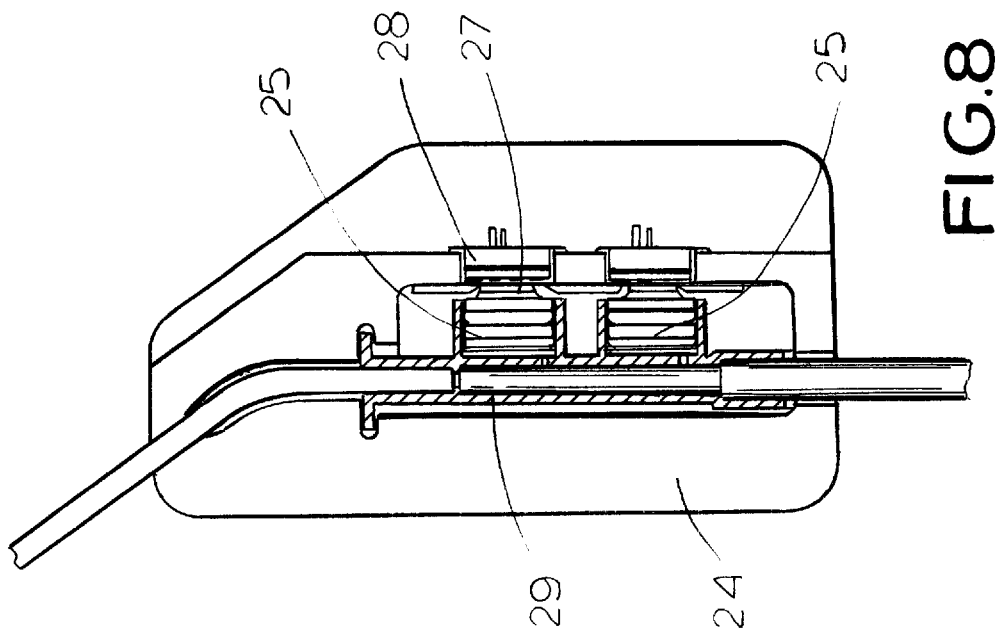
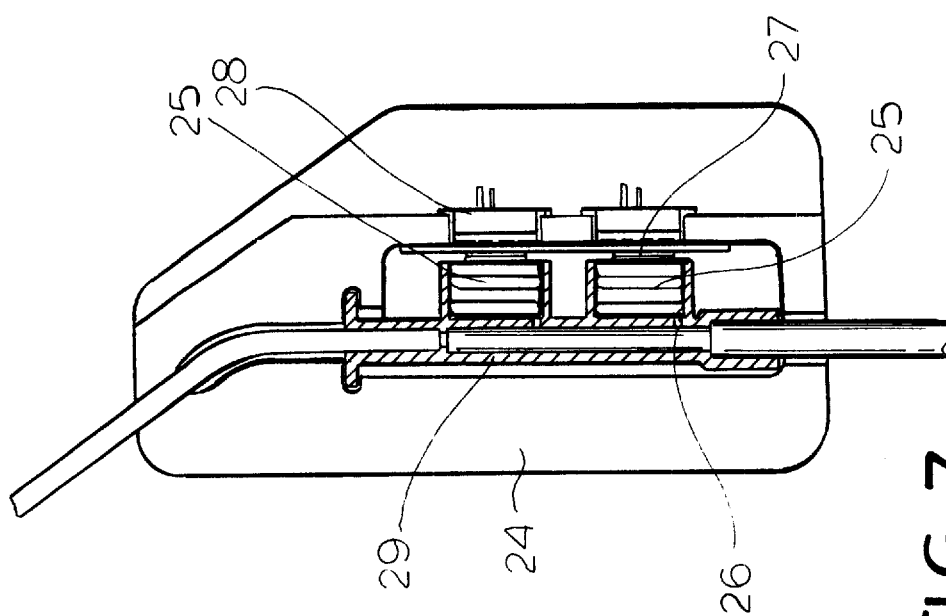

INJECTOR FOR APPLYING FLUIDS, ESPECIALLY CONTRAST AGENTS IN X-RAY AND NUCLEAR SPIN TOMOGRAPHY

CROSS REFERENCE TO RELATED APPLICATIONS

This application is a national stage of PCT/DE99/03795 filed Nov. 27, 1999 and based upon German national application 19900936.8 of Jan. 13, 1999 under the International Convention.

FIELD OF THE INVENTION

The invention relates to an injector for applying fluids, particularly contrast media for X-ray and nuclear spin tomography, with a tube system consisting of connecting tubes and a pump tube and with a plurality of storage vessels each connected via a connection tube as well as a branching piece to the pump tube leading to a cannula.

BACKGROUND OF THE INVENTION

In injectors known in practice several storage vessels are mounted on a frame of the injector and together can deliver a volume sufficient for the examination of a number of patients during a work day or a work shift, without requiring frequent interruptions during which the fluid has to be replaced the storage vessel has to be exchanged. This exchange process in itself is relatively cumbersome, since the storage vessel to be replaced has to be detached from the connection tube and, as a result air enters the connection tube and forms there an air bubble. The same problem also arises when the vessel runs empty during examinations, thereby allowing air to enter the connection tube, air which is not allowed to reach the patient and be injected into a vein, since this creates the risk of embolisms.

OBJECT OF THE INVENTION

It is therefore the object of the invention to provide an injector of the kind mentioned in the introduction so that the penetration of bubbles in the pump tube will be safely avoided at each operation stage, particularly also during the replacement of the storage vessels.

SUMMARY OF THE INVENTION

According to the invention the foregoing object is accomplished in an injector of the aforementioned kind in that to each connection tube a gas bubble detector as well as a valve are assigned and in that to the pump tube a pumping organ is assigned, which reverses the flow of fluid from the storage vessel to the cannula.

This injector has the advantage that the penetration of an air bubble into the connection tube, for instance when a storage vessel runs dry, is detected, after which by means of the valve assigned to the connection tube containing the air bubble, the connection tube is blocked and another connection tube can be turned open by means of its valve, so that the examination of the patient can continue without delay. Besides with the injector of the invention it is possible not only to detect the presence of the air bubble in the connection tube, but furthermore, after the replacement of the empty storage vessel with a full one, the pumping organ makes it possible to reopen the previously closed valve and to exert a pressure surge on the liquid existing in the pump tube and the connection tube which displaces the liquid upstream, whereby the air bubble is pushed back from the connection piece into the new storage vessel where it can rise to the surface, so that as a result the connection tube is continuously filled with liquid and the exchanged storage vessel can be used.

Within the framework of the invention it is further provided that the pump tube be associated with a roller pump for the active transport of the fluid from the storage vessel to the cannula. This has the advantage that gravity need not be relied upon to inject the fluid into the patient against the vein pressure, whereby furthermore the amount of fluid injected per given time unit can be varied by changing the rotary speed of the roller pump. The use of a roller pump has the particular advantage that no direct contact takes place between the fluid inside the pump tube and the roller pump, the sterility of the fluid being thus safeguarded at all times, and also ensuring that there is no danger of fluid contamination.

It has proven to be suitable when the gas bubble detector is formed by an ultrasound sender and receiver, by means of whose signals the associated valve can be switched. A gas bubble detector built in this way has sufficient precision and definition capability and delivers electric signals which can be used by conventional signal processing in order to switch the assigned valve.

Suitably the valves are formed by tube clips which narrow down the cross section of the connection tubes to the extent that no liquid can pass the same. The tube clips seizing the connection tubes from the outside have the advantages already mentioned in connection with the roller pump, that the sterility of the fluid is safeguarded at all times, since no components contact the fluid itself in order to interrupt the flow.

Within the framework of the invention it is provided that the tube clips have a prop pressing the connection tube against an abutment, thereby narrowing the cross section. The use of a prop for obstructing the fluid flow is more favorable than the use of a tube collar which can also be used in principle, but can not be readjusted so quickly and is subjected to higher wear.

For better monitoring of the injection process the tube clips have a switch detecting the position of the prop.

Further according to a particularly preferred embodiment within the framework of the invention, the pumping organ is provided with a correcting element adjacent to the pump tube, by means of which the pump tube can be deformed and the liquid existing inside the tube upstream of the correcting element can be pressed upstream. Again any direct contact with the fluid is avoided, since the pumping organ engages only the outside of the pump tube. Another advantage of this embodiment of the pumping organ consists in the simplicity of its mechanical construction, in the low cost of manufacture and its operational reliability. Due to the construction of the pumping organ it is also insured that the reversal of the fluid flow in the pump tube can be only short-term, i.e. no negative pressure can be generated in the tube system, which would exert an extended suction on the vein of the patient. The short-term pressure impulse created by the pumping organ is however sufficient for the minimal displacement of the upstream fluid column to the point that the air bubble which entered the connection tube is again removed from the same. Naturally, by accepting higher costs for the apparatus, it is also possible to assign a pumping organ to each connection tube instead of the pump tube.

The pumping organ has a particularly simple construction when the correcting element is formed by a unilaterally fastened W-shaped spring whose flank at the free end can be displaced from a rest position inclined with respect to the pump tube into a position running parallel with the pump tube and pressed against the pump tube. In this design of the correcting element, when the same is actuated the pump tube is at first deformed point by point and the fluid flow is stopped downstream, whereby during the subsequent pressing of the free flank the liquid upstream of the locked point is pressed in the direction of the storage vessel.

In principle it is possible to displace the freely hanging pump tube by means of the correcting element, until no further bending is possible and the clamping effect takes over. However it is better when on the side of the pump tube opposite to the correcting element a plate is arranged as an abutment, way the wear of the pump tube can then be reduced.

A two-arm lever can be provided for the adjustment of the correcting element. One arm of the lever in rest position can rest against the flank at the free end of the spring and its other arm can be coupled with a servo motor for the displacement of the correcting element.

A pressure chamber can be integrated in the tube system which is connected through at least one opening in the tube wall with the interior of the pump tube and can be filled with the fluid, and when the pressure chamber has a component which is adjustable under the effect of the fluid pressure and acts upon a pressure sensor. By monitoring the pressure in the tube system it is possible to determine how much fluid is actually being injected to the patient. Furthermore the pressure measurement represents a further safety device since, as a rule, disturbances during operation take effect always in the pressure existing in the tube system, for instance when due to a failure of the valves all connection tubes are closed and the pressure falls in the tube system, or when by using an unacceptable cannula whose cross section is too small the counterpressure increases excessively and therefore the pressure in the tube system also increases. Also leaks in the tube system are detected through a drop in pressure.

Since the pump tube to be used in combination with the roller pump has to be sufficiently elastic in order to convey the flow of fluid from the storage vessel to the cannula, which elasticity has a negative effect on the pressure measurement, between two segments of the pump tube a rigid pipe can be inserted, the rigid pipe having the opening to which the pressure chamber is attached.

In order to prevent a direct contact between the fluid and the pressure sensor, it is possible to simply use a fluid-proof, elastic membrane as the adjustable component.

Alternately it is possible to design the adjustable component as a piston tightened against the pressure chamber wall, which acts directly on the pressure sensor.

Since due to the pumping organ the fluid existing in the tube system is pushed upstream, at the downstream end of the tube system a suction is created. In order to securely prevent the patient's blood from entering the tube system, and to avoid replacing the entire tube system when the patient changes, so that absolute hygiene is insured, it is provided to make the pump tube of two parts, the part forming the free end having at least one check valve. In this embodiment it is insured that only the patient tube itself has to be replaced, while the rest of the tube system remains free of contamination, as has been proven during a hygiene check.

BRIEF DESCRIPTION OF THE DRAWING

The invention is described in greater detail below with reference to the drawing. In the drawing:

FIG. 7 is a side view of the pressure measuring system consisting of a pressure chamber and a pressure sensor, with a pressureless pressure chamber; and FIG. 8 is a view similar to FIG. 7 with the piston in maximal displacement.

SPECIFIC DESCRIPTION

Figure 1:
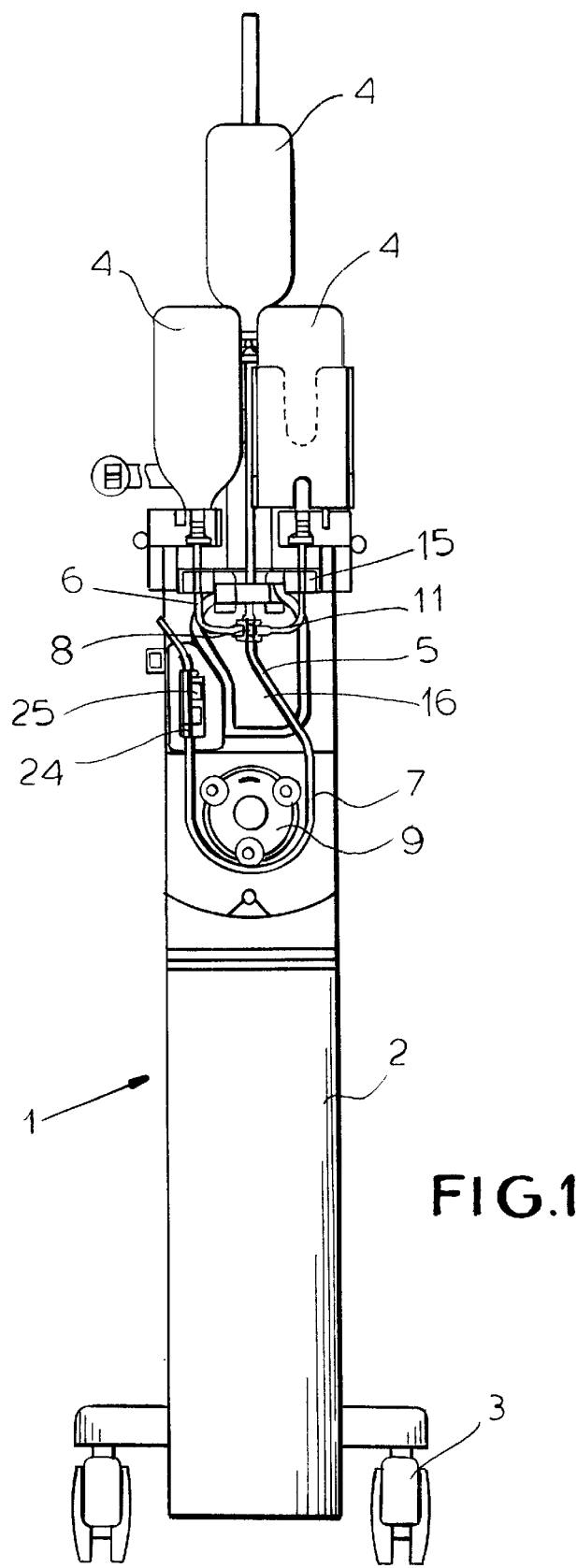
FIG. 1 is a perspective view of the injector according to the invention, with the storage vessels, the tube system and the roller pump.
Figure 2:
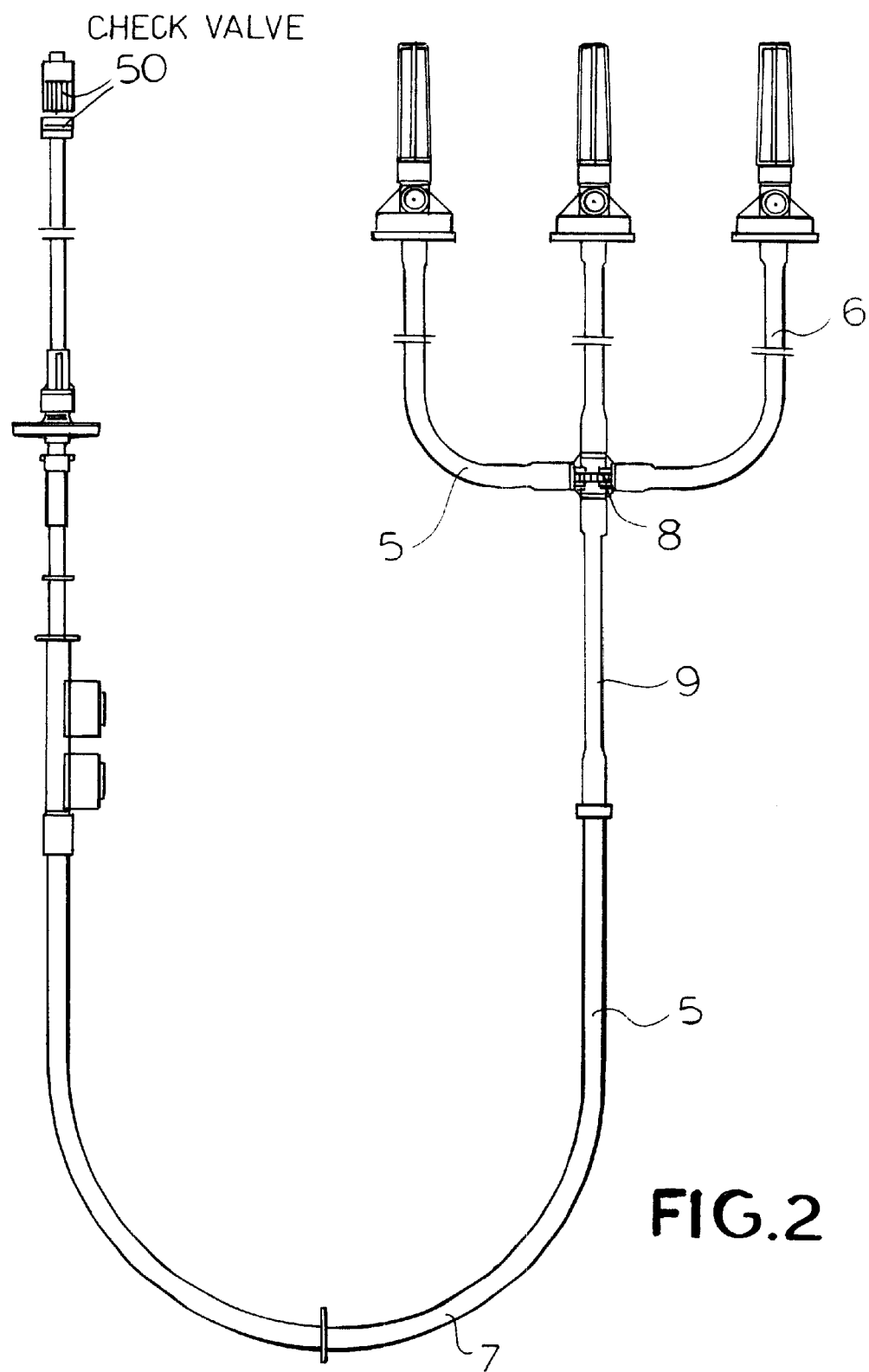
FIG. 2 is an elevational view of the tube system.

The injector 1 shown in the drawing serves particularly for applying of contrast media for X-ray and nuclear spin tomography examinations of patients, to whom over an extended period of time a contrast medium or alternately a NaCl rinsing solution has to be supplied continuously in constant or variable amounts. The injector 1 has a frame 2, which in the embodiment represented in the drawing is supported on rollers in a manner known Per se, but which can also be fastened to a support arm on the wall or the ceiling close to the examination device. On the frame 2 of the embodiment shown in the drawing three storage vessels 4 are mounted, from which fluid is supplied to the patient through a tube system 5. The tube system 5 consists of connection tubes 6 connected to the storage vessels 4, and a pump tube 7, which is coupled with the connection tube 6 via a branching piece 8.

Figure 3:
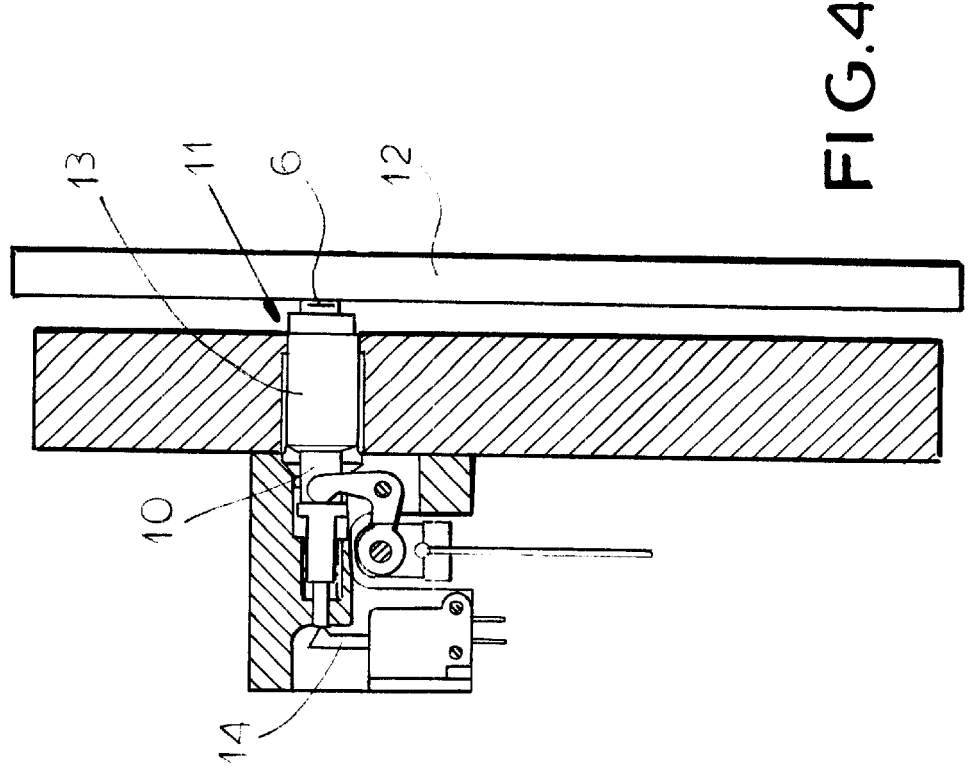
FIG. 3 is a cross sectional view of one of the connection valves assigned to the connection tubes of the tube system in open position.
Figure 4:
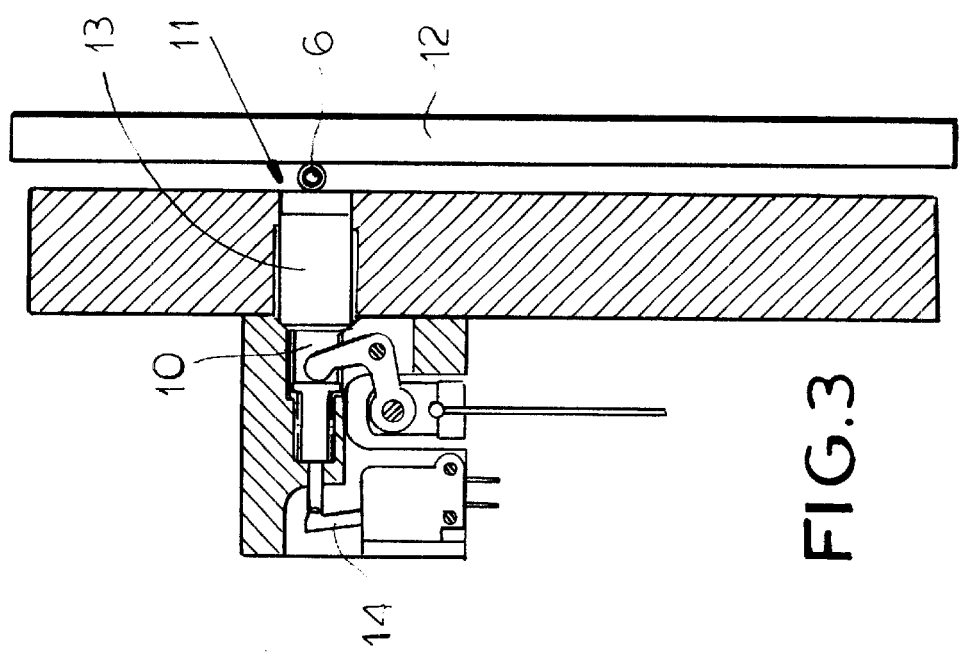
FIG. 4 is a cross sectional view of the valve of FIG. 3 in closed position.
Figure 5:
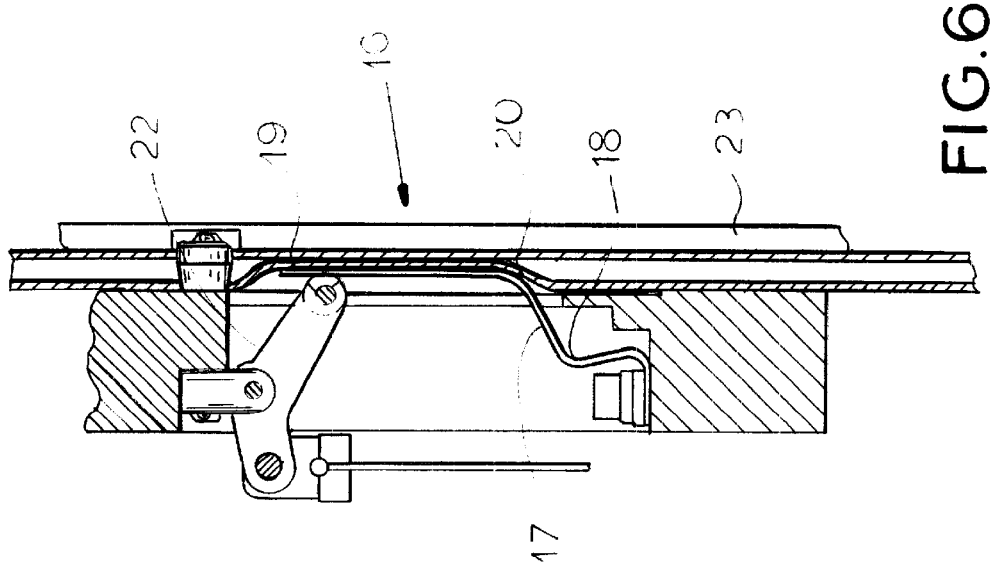
FIG. 5 is a cross sectional view of the W-shaped correcting element (seen from the side) of the pumping organ in rest position.
Figure 6:
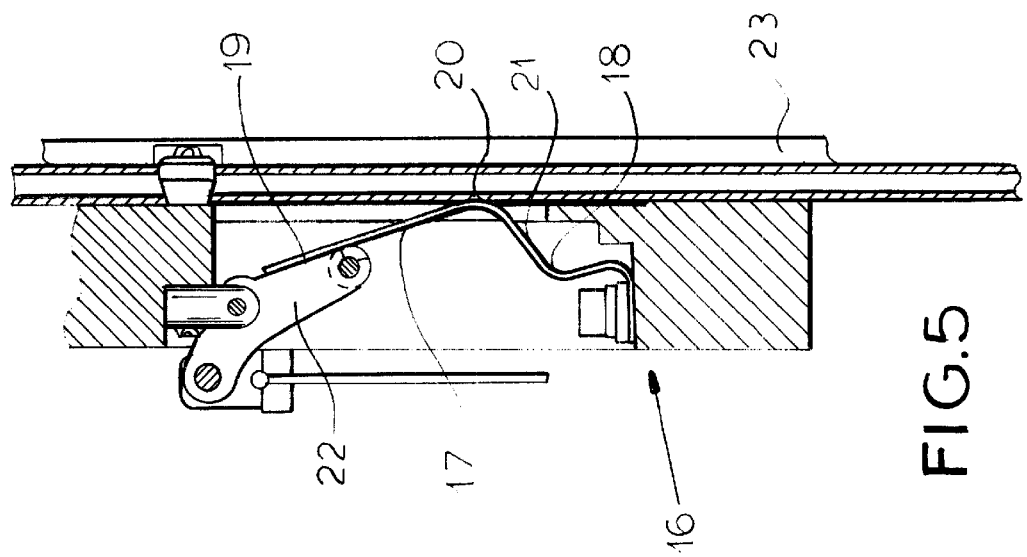
FIG. 6 is a cross sectional view corresponding to FIG. 5 with the correcting element of the pumping organ closing the pump tube.

By means of a roller pump 9 engaging at the outer circumference of the pump tube 7 without being in direct contact with the contrast medium, the latter is conveyed from the storage vessels 4 to the patient. In order to avoid a situation in which all storage vessels 4 can be empty at the same time, to each connection tube 6 a valve 11 formed by a tube clip 10 is assigned, which has a prop 13 pressing the connection tube 6 against an abutment 12, thereby closing the connection tube 6. The prop 13 is displaced by a motor from the position shown in FIG. 3 with open valve 11 to the closed position shown in FIG. 4. The position of the prop 13 is monitored by a switch 14 connected via signal lines with an evaluation and control unit which also switches the valve 11, the pumping organ 16 and the roller pump 9. With these valves 11 it is possible first to free a connection tube 6 and to remove fluid from the respective storage vessel 4, while the other two remain full. When the storage vessel 4 in use runs empty, an air bubble enters the connection tube 6. This air bubble is detected by an air bubble sensor 15, which is formed by an ultrasound sender and receiver. The electric signals generated by the sender are used to switch the valve 11 assigned to the connection tube 6, thereby preventing the further penetration of the air bubble. At the same time it is possible to open the valve 11 of the other storage vessel 4, thus insuring a continuous flow of fluid. The empty storage vessel 4 can now be simply replaced by a full one. However a simple switchback between the storage vessels 4 is not possible, because the air bubble is still in the connection tube 6 and would be transported further. In order to remove the air bubble from the tube system 5, a pumping organ 16 is assigned to the pump hose 7 which reverses the fluid flow from the storage vessel to the cannula, which has a correcting member 17 pressed against the pump tube 7, by means of which the pump tube 7 can be deformed and inside the pump tube 7 the fluid existing upstream of the correcting element can be pressed upstream. The fluid column existing in the pump tube 7 and in the connection tube 6 is thus displaced by the pumping organ 16 in the direction of the storage vessel 4, so that the air bubble exits the connection tube 6 and enters the storage vessel 4 where it rises to the surface, so that there is nothing left to prevent the connection tube 6 and the storage vessel 4 from being used again. The pumping organ 16 is shown in detail in FIGS. 5 and 6. The correcting element 17 is formed by a unilaterally fastened W-shaped spring 18, which is fixed at one end. The flank 19 arranged at the free end can be displaced from a rest position inclined towards the pump tube 7, wherein it lies against the pump tube 7 only with the bend 20 connecting it to the neighboring flank 21, into a position in which the flank 19 runs parallel to the pump tube 7, wherein by means of a two-arm lever 22 it presses the pump tube 7 against a plate 23 acting as an abutment. Thereby it has to be noted that in the initial displacement of the spring 18 at first the pump tube 7 is clamped and in the subsequent displacement the fluid upstream of the clamping point is displaced by the free flank 19 of the spring 18 in the direction of the storage vessel 4. A servo motor is connected with the second arm of the two-arm lever 22.

In order to be able to constantly monitor the pressure ratio in the tube system 5, a pressure-measuring system 24 (FIGS. 7 and 8) with a pressure chamber 25 is integrated in the tube system 5. The pressure chamber is connected through an opening 26 in the tube wall with the interior of the pump tube 7 and can be traversed by the flow of fluid, whereby the pressure chamber 25 has a component 27 adjustable under the effect of the fluid pressure and acting on the pressure sensor 28 which detects the pressure ratio. The pressure chamber 25 is fastened to a rigid tube 29 with the opening 26, inserted between the two segments of the pump tube 7.

In an embodiment not shown in the drawing the adjustable component is formed by a fluid-proof, elastic membrane. while in the embodiment shown in the drawing the adjustable component 27 is built as a piston tightened against the pressure chamber wall which acts directly on the pressure sensor 28 and has the advantage of a bigger adjustment path, thereby making possible a higher precision of the measurement.

The tube system 5 is further built so that the pump tube 7 is made in two parts, whereby the part forming the free end has a check valve 50 preventing the patient's blood from entering the tube system 5.

I claim:
1. An injector for supplying a liquid to a patient, comprising:
   a plurality of storage vessels;
   a tube system connecting said vessels with a cannula, said tube system comprising:
      respective connection tubes each connected to one of said vessels,
      a pump tube connected with said cannula, and
      a branching piece between said pump tube and said connection tubes;
   a respective gas bubble detector for each connection tube responsive to movement of a gas bubble from the respective storage vessel into the respective connection tube;
   a respective valve for each connection tube selectively operable to block and unblock liquid movement through the respective connection tube; and
   a pumping organ along said pump tube for reversing flow of liquid along said pump tube to drive a gas bubble back into a respective storage vessel, said pumping organ having a correcting element lying against said pump tube for deflecting a wall of said pump tube to drive liquid therein in an upstream direction.

2. The injector defined in claim 1 wherein said correcting element is formed by a W-shaped spring having a flank at a free end displaceable from a rest position inclined relative to said pump tube in a position parallel to said pump tube and pressed against said pump tube.

3. The injector defined in claim 2, further comprising an abutment on an opposite side of said pump tube from said correcting element.

4. The injector defined in claim 2, further comprising a two-arm-lever having one arm lying against said flank in the rest position and another arm coupled with a servomotor for displacement of the correcting element.

5. The injector defined in claim 1, further comprising a roller pump engaging said pump tube for pumping said liquid from one of the storage vessels of the cannula.

6. The injector defined in claim 1 wherein each of said gas bubble detectors is formed by an ultrasound sender and receiver for switching the respective valve for each connection tube.

7. The injector defined in claim 1 wherein each of said valves is formed by a respective tube clip.

8. The injector defined in claim 7 wherein each of said tube clips has an adjustable prop pressing the respective connection tube against an abutment.

9. The injector defined in claim 8 wherein each tube clip has a switch for detecting the position of the respective prop.

10. An injector for supplying a liquid to a patient, comprising:
- a plurality of storage vessels;
- a tube system connecting said vessels with a cannula, said tube system comprising:
  - respective connection tubes each connected to one of said vessels,
  - a pump tube connected with said cannula, and
  - a branching piece between said pump tube and said connection tubes;
- a respective gas bubble detector for each connection tube responsive to movement of a gas bubble from the respective storage vessel into the respective connection tube;
- a respective valve for each connection tube selectively operable to block and unblock liquid movement through the respective connection tube;
- a pumping organ along said pump tube for reversing flow of liquid along said pump tube to drive a gas bubble back into a respective storage vessel;
- a pressure chamber integrated in said connection tube and communicating with said pump tube through at least one opening in a wall of said pump tube and adapted to be filled with liquid from said pump tube; and
- a component in said pressure chamber adjustable by fluid pressure therein and acting upon a pressure sensor.

11. The injector defined in claim 10 wherein said pump tube includes a pair of flexible tube segments between which a rigid pipe is inserted, said pressure chamber being connected with said rigid pipe and said opening being formed in said rigid pipe.

12. The injector defined in claim 10 wherein said component is a fluid-tight elastic membrane.

13. The injector defined in claim 10 wherein said component is a piston slidable in said pressure chamber and acting directly on said pressure sensor.

14. The injector defined in claim 10, further comprising an electric valve on a free end of said pump tube.

* * * * *